Nov. 17, 1970 F. W. ANDERSON Plant Pat. 3,000
NECTARINE TREE
Filed Oct. 17, 1968
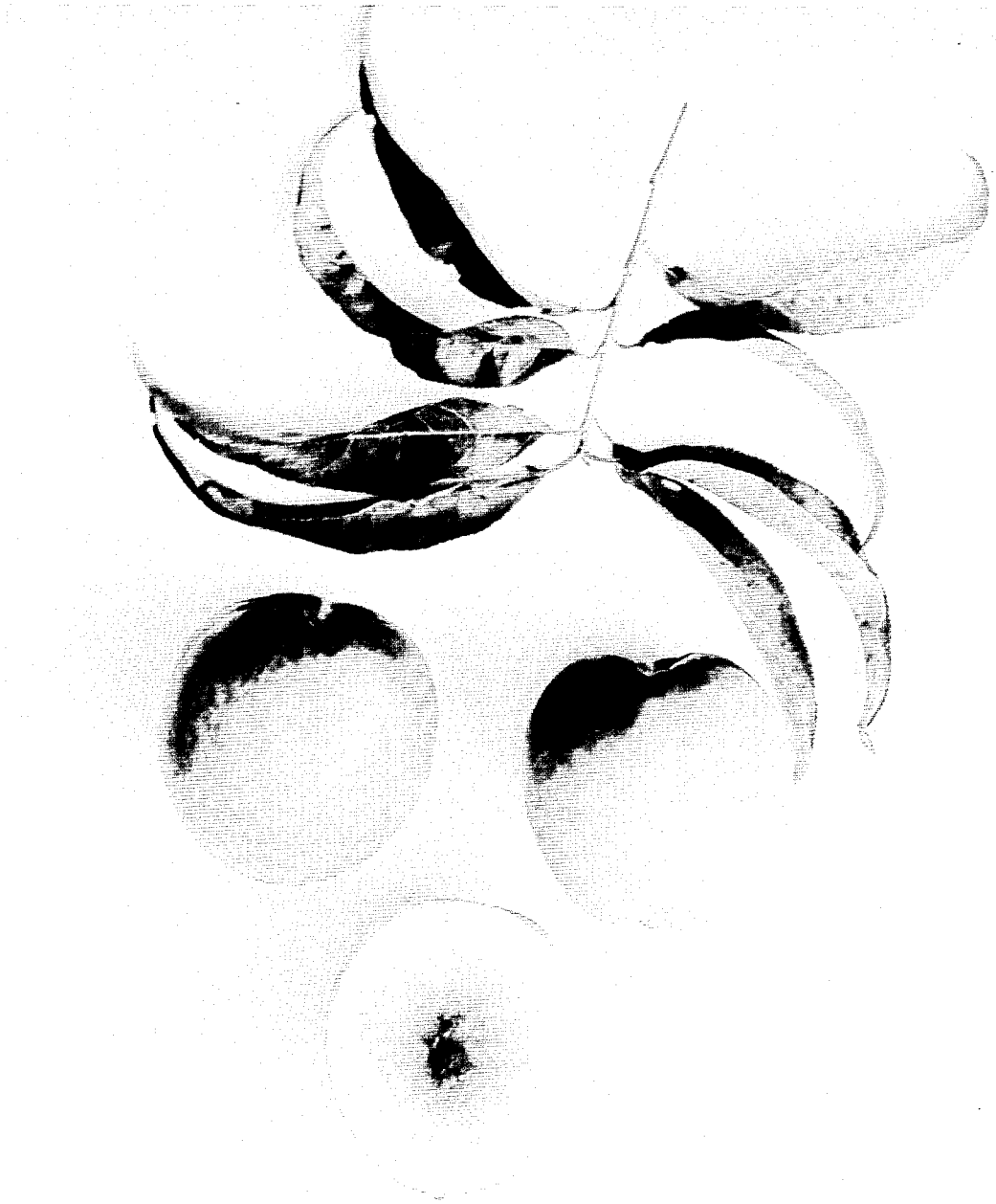
INVENTOR
Frederic W. Anderson
BY
Webster & Webster
ATTORNEYS United States Patent Office Plant Pat. 3,000
Patented Nov. 17, 1970

3,000
NECTARINE TREE

Frederic W. Anderson, Merced, Calif., assignor to Reedley Nursery, Inc., Reedley, Calif., a corporation of California Filed Oct. 17, 1968, Ser. No. 768,561
Int. Cl. A01h 5/03
U.S. Cl. Plt.—41 1 Claim

ABSTRACT OF THE DISCLOSURE

A variety of nectarine tree which is of vigorous, open, and spreading growth, and a regular and productive bearer of uniform, large, globose to slightly oblong clingstone fruit having yellow flesh, and yellow skin substantially overspread with a bright red.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The herein claimed new and distinct variety of nectarine tree was originated by me, in my experimental orchard located as aforesaid, as a second-generation seedling of a cross between Red Grand (U.S. Plant Pat. No. 1,060) nectarine, and an unnamed seedling (unpatented) whose fruit fails to ripen under the climatic conditions of the Central Valley of California.

When such second-generation seedling bore fruit and evidenced novel and commercially desirable characteristics, I selected it for asexual reproduction, preparatory to introduction to the trade.

ASEXUAL REPRODUCTION OF THE VARIETY

Subsequent to origination and selection by me of the present variety of nectarine tree, in the manner above described, I asexually reproduced it by top-working on mature nectarine trees in my said experimental orchard, and in maturity such reproductions ran true to the original tree in all respects.

SUMMARY OF THE VARIETY

The herein claimed variety of nectarine tree is of large to medium size, vigorous, open, and spreading in growth, and a regular and productive bearer of uniform, large, globose to slightly oblong clingstone fruit having yellow flesh, and yellow skin substantially overspread with bright red; the variety, in comparison to the Late Le Grand (U.S. Plant Pat. No. 1,035) nectarine, having general resemblance in tree and fruit including substantially the same ripening period, but being distinctively characterized by fruit whose flesh is more melting and hence of better eating quality, and whose skin is smoother, and with the overspreading red brighter and more attractive.

BRIEF DESCRIPTION OF THE DRAWING

The drawing is an illustration, by photographic reproduction in color, of fruit and leaves of the variety; a portion of one fruit being removed, by a chordal cut, to expose and show the flesh, the stone remaining in place below the cut.

DESCRIPTION OF THE VARIETY

The botanical details of this new and distinct variety of nectarine tree—with color definitions referenced to Maerz and Paul Dictionary of Color—are as follows:

Tree:
- *Size.*—Large to medium.
- *Vigor.*—Vigorous.
- Growth.—Spreading.
- *Density.*—Open.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Large. Average length: 6"–7". Average width: 1¾"–2".
- *Form.*—Lanceolate.
- *Thickness.*—Medium.
- *Texture.*—Smooth.
- *Margin.*—Crenate.
- *Petiole.*—Medium length—average ½".
- *Glands.*—Number and position: Usually 2 on blade, and 2 or 3 on petiole. Alternate. Medium size. Reniform.
- *Color.*—Top side: Medium green (23–L–7). Under side: Lighter green (22–L–6).

Flower buds:
- *Length.*—Medium.
- *Form.*—Plump.

Flowers:
- *Blooming period.*—Medium, as compared with other variaties.
- *Size.*—Large. Shorery.

Fruit:
- *Maturity when described.*—Eating ripe: Aug. 15, 1968.
- *Date of first picking.*—Aug. 5, 1968.
- *Date of last picking.*—Aug. 15, 1968.
- *Size.*—Uniform. Large. Average diameter axially: 2½"–3¼". Average transversely in suture plane: 2½"–3½".
- *Form.*—Uniform. Symmetrical. Globose to slightly oblong.
- *Suture.*—Shallow, with slight depression beyond pistil point.
- *Ventral surface.*—Rounded slightly.
- *Lips.*—Equal.
- *Cavity.*—Rounded. Average depth: ⅜". Average breadth: ¾".
- *Base.*—Rounded.
- *Apex.*—Depressed.

Skin:
- *Thickness.*—Medium.
- *Texture.*—Medium.
- *Tenacity.*—Tenacious to flesh.
- *Down.*—Wanting.
- *Color.*—Yellow (10–L–5) substantially overspread with bright red (5–L–5) shading to darker red (7–L–6); the red—to a great extent—being mottled.

Flesh:

*Juice.*—Moderate. Rich.
*Texture.*—Firm. Meaty. Melting.
*Fibers.*—Abundant.
*Ripens.*—Evenly.
*Flavor.*—Subacid. Delicate.
*Aroma.*—Distinct.
*Eating quality.*—Good to best.
*Color.*—Yellow (10–K–5). Surface of pit cavity: Red (6–L–6) with the red streaked into the flesh.

Stone:

*Type.*—Cling.
*Size.*—Large to medium. Average length: 1⅛". Average breadth: 1". Average thickness: ⅝".
*Form.*—Oval.
*Base.*—Oblique.
*Hilum.*—Broad. Oval.
*Apex.*—Rounded.
*Sides.*—Equal.
*Surface.*—Irregularly furrowed and pitted throughout.
*Dorsal edge.*—Full, with deep broad groove.
*Tendency to split.*—Slight.
*Color.*—Garnet red (7–L–6).

Use: Market-local and long distance shipping. Dessert.
Keeping Quality: Good.
Shipping Quality: Good.

The nectarine tree and its fruit herein described may vary in slight detail due to climatic and soil conditions under which the variety may be grown; the present description being of the variety as grown in the Central Valley of California.

What is claimed is:

1. A new and distinct variety of nectarine tree, substantially as illustrated and described, which is of large to medium size, vigorous, open, and spreading in growth, and a regular and productive bearer of uniform, large, globose to slightly oblong clingstone fruit having yellow flesh, and yellow skin substantially overspread with bright red; the variety, in comparison to the Late Le Grand nectarine, having general resemblance in tree and fruit including substantially the same ripening period, but being distinctively characterized by fruit whose flesh is more melting and of better eating quality, and whose skin is smoother, and with the overspreading red brighter and more attractive.

No references cited.

ROBERT E. BAGWILL, Primary Examiner